US005763353A

United States Patent [19]
Kadono et al.

[11] Patent Number: 5,763,353
[45] Date of Patent: Jun. 9, 1998

[54] HYDROGENATION CATALYST PRECURSOR, HYDROGENATION CATALYST AND PRODUCTION PROCESS FOR ALCOHOLS

[75] Inventors: Yasuo Kadono; Yasuyuki Hattori; Masamitsu Horio; Fumihiko Nakamura, all of Wakayama, Japan

[73] Assignee: Kao Corporation, Tokyo, Japan

[21] Appl. No.: 789,540

[22] Filed: Jan. 27, 1997

[30] Foreign Application Priority Data

Feb. 15, 1996 [JP] Japan .................................. 8-027757

[51] Int. Cl.$^6$ .................................................. B01J 23/72
[52] U.S. Cl. .......................... 502/331; 502/329; 568/799; 568/864
[58] Field of Search ........................ 568/799, 864; 502/329, 331

[56] References Cited

U.S. PATENT DOCUMENTS

| 4,278,567 | 7/1981 | Miya et al. | 502/331 |
| 4,386,018 | 5/1983 | Merger et al. | 252/465 |
| 5,120,700 | 6/1992 | Matsuda et al. | 502/329 |
| 5,243,095 | 9/1993 | Roberts et al. | 568/874 |
| 5,302,568 | 4/1994 | Matsuda et al. | 502/331 |

FOREIGN PATENT DOCUMENTS

| 55-31428 | 3/1980 | Japan . |
| WO 86/06090 | 10/1986 | WIPO . |

OTHER PUBLICATIONS

George Calingaert, et al., "Small–Plant–Scale Liquid Phase Hydrogenation under High Pressure", Industrial and Engineering Chemistry, vol. 26, No. 7, (1934), pp. 878–880.

*Primary Examiner*—C. Warren Ivy
*Assistant Examiner*—Garth M. Dahlen
*Attorney, Agent, or Firm*—Oblon, Spivak, McClelland, Maier & Neustadt, P.C.

[57] ABSTRACT

The present invention provides a hydrogenation catalyst precursor which does not bring about a problem of environmental pollution involved in copper-chromium catalysts and has a high activity, a high durability and a high selectivity as compared with those of conventional copper-iron-aluminum catalysts, a hydrogenation catalyst obtained by reducing the same, and a production process for alcohols using the above hydrogenation catalyst. The hydrogenation catalyst precursor described above comprises copper, iron and aluminum and containing as a principal component a compound oxide of copper, iron and aluminum in which an atomic ratio Cu:Fe:Al is 1:(0.02 to 0.4):(1.0 to 4.0) and which has a copper-aluminum spinel structure.

18 Claims, No Drawings

HYDROGENATION CATALYST PRECURSOR, HYDROGENATION CATALYST AND PRODUCTION PROCESS FOR ALCOHOLS

[FIELD OF THE INVENTION]

The present invention relates to a hydrogenation catalyst precursor, a hydrogenation catalyst obtainable by using the same and a production process for alcohols using the above hydrogenation catalyst.

[RELATED PRIOR ART]

A lot of processes have so far been disclosed since 1930 regarding processes for hydrogenating organic carboxylic acids or organic carboxylic esters to produce aliphatic alcohols, alicyclic alcohols or aromatic alcohols. However, it is noted that severe conditions are required for the production of higher aliphatic alcohols. In industrially available processes, hydrogenation is carried out in the conditions of such high temperatures and high pressures as 200° to 300° C. and 200 to 300 atms (hydrogen pressure) usually using a copper-chromium catalyst. The copper-chromium catalyst is usually called a copper chromite catalyst, and a production method thereof has not advanced to a large extent from the method described in "Industrial and Engineering Chemistry" vol. 26, pp. 878 (1934).

Since this catalyst contains harmful chromium, prudent attention is required in handling it, and a great deal of labor is spent in treating/recovering the waste catalyst.

Copper-aluminum oxide catalysts have so far been paid attentions as an alternative to the copper-chromium catalyst. The copper-aluminum oxide catalysts are produced by a method in which an aqueous solution of an acid copper salt such as copper nitrate or copper sulfate is mixed with that of an acid aluminum salt such as aluminum nitrate or aluminum sulfate; this mixed solution is reacted with an alkaline aqueous solution of sodium carbonate, sodium hydroxide or potassium hydroxide to precipitate a mixture of metal hydroxides; and this precipitate is washed and dried, followed by calcining. Accordingly, the copper-aluminum oxide catalysts have the advantage that harmful substances are not involved in the production process. However, those copper-aluminum oxide catalysts produced by conventional methods have the defects that they have lower activities as compared with those of the copper-chromium catalysts and that reduced copper particles which are active species coagulate to be rapidly deactivated in ordinary use conditions.

It is described in JP-B-55-41815 that, in order to solve this problem, a high activity is revealed by maintaining copper oxide and aluminum oxide in a homogeneous mixed state, wherein an ammonium salt which forms an ammine complex with a copper ion is used as a buffer, and a sodium aluminate aqueous solution containing sodium hydroxide is reacted with an acid copper salt aqueous solution in the presence of the buffer described above. However, it is insufficient for controlling coagulation of reduced copper particles, and there is the defect that the catalyst life is short in the production of higher alcohols where the production conditions are severe. Thus, catalysts residing in a practicable level out of catalysts comprising copper-aluminum oxide are not available yet.

A hydrogenation catalyst which has a specific surface area of 50 to 120 m$^2$/g, all or a part of which is crystal having a copper-aluminum spinel structure and which contains copper in the form of oxide is disclosed in JP-B-2-22051 equivalent to EP-A- 44444. However, it is a catalyst for use in producing propanediol at a pressure of 300 bar or lower and hydrogenation temperatures of 50° to 200° C. and is not used for the production of higher alcohols where the reaction is carried out at 200° C. or higher and the reaction conditions are severer. Further, in the case where it is used in a suspension process in the production of higher alcohols, there is the problem that the filtering property and the ether selectivity are inferior, and in the case where it is used in a fixed bed process, there is the problem that the durability is inferior.

Further, various copper-iron-aluminum catalysts are proposed as ternary catalysts containing iron in addition to copper and aluminum (JP-B-58-50775 equivalent to U.S. Pat. No. 4,278,567 and JP-B-6-22677 equivalent to U.S. Pat. No. 5,120,700). However, the copper-iron-aluminum catalysts obtained by the methods described in the above publications reside in the same level as that of the copper-chromium catalyst in terms of activity, selectivity and durability, but further increase in the activity is desired in order to elevate the productivity and make the reaction conditions milder.

[SUMMARY OF THE INVENTION]

Accordingly, an object of the present invention is to provide a hydrogenation catalyst precursor which does not bring about a problem of environmental pollution involved in copper-chromium catalysts and has a high activity, a high durability and a high selectivity as compared with those of conventional copper-iron-aluminum catalysts, a hydrogenation catalyst obtained by using the same, and a production process for alcohols using the above hydrogenation catalyst.

Intensive investigations made by the present inventors in order to solve the problems described above have resulted in achieving a high activity, a high durability and a high selectivity, which have not been attained by conventional copper-aluminum oxide catalysts and copper-iron-aluminum catalysts, by preparing a hydrogenation catalyst precursor comprising a specific amount of iron oxide and containing a compound oxide having a copper-aluminum spinel structure as a principal component, and thus completing the present invention.

That is, the present invention relates to a hydrogenation catalyst precursor comprising copper, iron and aluminum and containing as a principal component a compound oxide of copper, iron and aluminum in which an atomic ratio Cu:Fe:Al is 1:(0.02 to 0.4):(1.0 to 4.0) and which has a copper-aluminum spinel structure, a hydrogenation catalyst obtained by reducing the same, and a production process for alcohols, characterized in that organic carboxylic acid and/or organic carboxylic ester is reduced by hydrogen in the presence of the above hydrogenation catalyst.

Further, the present invention relates to said hydrogenation catalyst precursor, wherein copper atoms constituting the copper-aluminum spinel structure have a proportion exceeding 65% by weight based on the total weight of copper atoms contained in the hydrogen catalyst precursor, the hydrogenation catalyst, and the production process for alcohols.

Also, the present invention relates to said hydrogenation catalyst precursor further comprising barium and/or zinc and having an atomic ratio Cu:Ba:Zn of 1:(0 to 2.0):(0 to 2.0), the hydrogenation catalyst, and the production process for alcohols.

Further, the present invention relates to said hydrogenation catalyst precursor obtainable by a solid phase reaction of copper oxide with aluminum oxide at calcining temperatures of 500° to 1500° C., the hydrogenation catalyst, and the production process for alcohols.

Furthermore, the present invention relates to use of preceding catalyst for catalytic reduction of an organic carboxylic acid and/or an organic carboxylic ester with hydrogen gas.

[DETAILED DESCRIPTION OF THE INVENTION]

The hydrogenation catalyst precursor and the production process for the same are explained in detail below.

The production process for the hydrogenation catalyst precursor of the present invention shall not specifically be restricted, and conventional methods including a coprecipitation method, a kneading method and an alkoxide method can be applied. It is prepared, for example, by drying and calcining a precipitate obtained by the coprecipitation method in which a precipitant is added to a mixed solution of respective metal salts which are turned into a copper-aluminum spinel and a compound oxide, or by the kneading method in which respective compounds such as oxides, hydroxides, carbonates, and nitrates are uniformly mixed and calcined. In the case where the above catalyst is prepared by the coprecipitation method, any forms of the metal salts can be used as long as they are water soluble. In general, sulfates, nitrates, ammonium complex salts, acetates, or chlorides are used. Alkaline aqueous solutions of ammonia, urea, ammonium carbonate, sodium hydrogencarbonate, sodium carbonate, and sodium hydroxide are used as the precipitant.

Further, trace components of graphite, fatty acid salts, starch, mineral oils, talc, alkaline metal salts, and alkaline earth metal salts may be added in order to elevate a mechanical strength of the hydrogenation catalyst as long as the effects of the present invention are not damaged.

In the case where the hydrogenation catalyst precursor is prepared by the coprecipitation method, it is important to select a pH in preparing and calcining temperatures. For example, the pH in preparing is preferably 8 to 12. The calcining temperatures are 500° to 1500° C., preferably 600° to 1000° C. under an oxidative atmosphere in which oxygen is present in calcination.

The hydrogenation catalyst precursor of the present invention may be supported on a carrier or may be mixed with a carrier (in this case, the carrier is called a diluent carrier). The carrier includes usually available ones such as diatomaceous earth, alumina, silica gel, magnesia, silica-magnesia, calcia, zirconia, titania, zeolite, and silica-alumina. A production method therefor shall not be restricted. Among them, alumina is particularly preferred.

The carrier such as alumina, magnesia, zirconia, and titania may have not only the form of oxide but also the forms of hydrate such as hydrogel and hydroxide. The amount of the catalyst shall not specifically be restricted and is preferably 10 to 100% by weight in terms of a proportion of the catalyst component based on the carrier. The carrier described above may be used as a diluent carrier. In this case, the amount of the diluent carrier is preferably 0.1 to 50% by weight based on the weight of the hydrogenation catalyst precursor. The hydrogenation catalyst precursor obtained may be used in the form of powder or can be used by molding it according to reaction manners.

The present invention is characterized in that the hydrogenation catalyst precursor comprises a specific amount of iron oxide together with a compound oxide having a copper-aluminum spinel structure as a principal component. A characteristic crystalline structure of copper-aluminum spinel reveals a fine distribution and a configuration of copper and aluminum and is the same as the spinel structure shown in "Crystal Engineering Handbook" (Oct. 1, 1981, third edition, pp. 47, Kyoritsu Shuppan). This specific crystalline structure is formed by a solid phase reaction of copper oxide with aluminum oxide. In the method described above, the calcining temperatures are 500° to 1500° C., preferably 600° to 1000° C. In the case where the calcining temperatures are high, the specific surface area of the hydrogenation catalyst precursor is reduced, and the catalyst activity is lowered.

The copper-aluminum spinel structure can be confirmed by investigating an atomic arrangement by Extended X-ray Absorption Fine Structure method (hereinafter abbreviated to an EXAFS method). It can easily be confirmed by X-ray diffraction method. In the X-ray diffraction method, the copper-aluminum spinel is characterized by peaks corresponding to the lattice spacings d of 2.436, 2.856 and 1.4278 [described in a card number 33-448 of Powder Diffraction File published by Joint Committee on Powder Diffraction Standards (hereinafter abbreviated to JCPDS)]. Copper and iron which are the constituents of the hydrogenation catalyst form a spinel structure (copper-iron spinel) as well. Since the copper-iron spinel gives peaks characterized by the lattice spacings d of 2.502, 2.985 and 1.492 (described in a card number 34-425 of JCPDS Powder Diffraction File), it can readily be distinguished from the copper-aluminum spinel. However, the amount of the copper-aluminum spinel present in the hydrogenation catalyst precursor containing copper atoms can not be determined by the X-ray diffraction method. Therefore, the amount of the copper-aluminum spinel contained in the hydrogenation catalyst precursor of the present invention has been determined by means of X-ray Absorption Near Edge Structure method (hereinafter abbreviated to an XANES method) (X-ray Absorption, D. C. Koningsberger & R. Prins, John Willey & Sons (1988)).

The XANES method is an analytical method making use of an X-ray absorption fine structure and makes use of the fact that "elements have specific characteristic absorption edge in X-ray regions, and inner-shell electrons are released in the form of photo-electrons by absorbing energy more than the absorptivity, whereby fine structures appear in X-ray absorption spectra of inner-shell excitation". The EXAFS method in which information regarding an atomic arrangement is obtained by analyzing a vibration structure appearing in a high energy side (near 1000 eV) is famous as a method making use of an X-ray absorption fine structure. On the other hand, in the XANES method, an absorption fine structure appearing in the vicinity (<30 to 50 eV) of an absorption edge is utilized. Since this absorption fine structure reflects an electronic state of an element absorbing an X-ray, a condition of each element can be identified by using a position of an absorption edge and a form in the vicinity thereof. That is, if an attention is focused on a copper element, information regarding a condition of copper is obtained.

In the present invention, a condition of copper contained in the hydrogenation catalyst precursor has been acknowledged by this method. When coppers of two or more kinds of conditions are supposed to be present, waveform separation is carried out to divide them into XANES of a standard sample, whereby a percentage of copper atoms forming copper-aluminum spinel based on copper atoms contained in the hydrogenation catalyst precursor has been determined.

It is important to settle a composition ratio of the hydrogenation catalyst precursor at an atomic ratio Cu:Fe:Al of 1:(0.02 to 0.4):(1.0 to 4.0). If the atomic ratio of the hydrogen catalyst precursor falls in this range, the catalyst not only reveals a high activity and a high selectivity but also provides improved filterability which is important when the catalyst is used in a suspension process.

Alcohols obtained by using a catalyst prepared by reducing a catalyst precursor containing no iron include a lot of hydrocarbons formed by dehydration of resulting alcohols and ether compounds formed by dehydration condensation of two molecules of alcohols. Among them, the content of the ether compounds is markedly large, being a problem in terms of selectivity. Also, there is the problem that, since a part of copper atoms remain in the form of CuO, the metallic copper is deposited on the inner surface of a high pressure hydrogen reactor when alcohols are produced with the hydrogenation catalyst obtained by reducing the hydrogenation catalyst precursor. Further, in the case where the catalyst is used in a suspension process, a filterability of the catalyst is notably inferior as compared with that of the hydrogenation catalyst precursor of the present invention, which being a problem in practical use.

Copper-aluminum spinel is formed by a solid phase reaction of copper oxide with aluminum oxide. Normally, since iron oxide reacts with copper oxide to form copper-iron spinel, addition of iron decreases the amount of the copper-aluminum spinel. However, in the case where iron is contained as the third component in a relatively small amount, namely in a proportion Cu:Fe:Al of 1:(0.02 to 0.4):(1.0 to 4.0) in terms of an atomic ratio, a solid phase reaction of copper oxide with aluminum oxide is accelerated. This provides the characteristic that a proportion of copper atoms forming the copper-aluminum spinel based on the whole copper atoms contained in the hydrogenation catalyst precursor is increased. On the other hand, in the case where an atomic ratio of iron to copper exceeds 0.4, the high activity can not be achieved while the selectivity is good.

In the case where an atomic ratio of aluminum in the hydrogenation catalyst precursor of the present invention is less than 1, the hydrogenation catalyst precursor has the defect that since a proportion of aluminum atoms forming the copper-aluminum spinel based on copper atoms contained in the hydrogenation catalyst precursor is small, the activity is reduced. On the other hand, in the case where an atomic ratio of aluminum exceeds 4, the amount of the copper-aluminum spinel formed has no problems but a proportion of active effective components in the hydrogenation catalyst is reduced, and therefore the intended catalyst activity can not be obtained.

Further, barium and/or zinc may be contained as the fourth component other than copper, iron and aluminum in a proportion Cu:Ba:Zn of 1:(0 to 2.0):(0 to 2.0) in terms of an atomic ratio based on copper. Alcohols obtained by using the catalyst prepared by reducing the hydrogenation catalyst containing barium and/or zinc have the advantages that the contents of hydrocarbons formed by dehydration of alcohols and ether compounds formed by dehydration condensation of two molecules of alcohols are decreased and the alcohol yields are increased.

(Reduction of the hydrogenation catalyst precursor)

The hydrogenation catalyst of the present invention is used for hydrogenating organic carboxylic acids and/or organic carboxylic esters to produce alcohols and can be obtained by reducing the hydrogenation catalyst precursor described above. When reducing the hydrogenation catalyst precursor, any method of vapor phase reduction and liquid phase reduction carried out in a solvent such as hydrocarbons including liquid paraffin, dioxane, aliphatic alcohols, and fatty esters may be used. For example, in the case where the reduction is carried out using hydrogen gas, it is preferably carried out until formation of water is not observed or absorption of hydrogen is not observed. In particular, in the case where the reduction is carried out in a solvent, it is preferably carried out until absorption of hydrogen is not observed at temperatures of 150° to 350° C. Further, in the case where the hydrogenation catalyst precursor is reduced in organic carboxylic acid and/or organic carboxylic ester which are raw materials for alcohols, no problems are involved in using a conventional catalyst activating method in which the hydrogenation catalyst precursor is heated in a hydrogen atmosphere to reduce it and then used for the reaction as it is. A reducing agent used here includes, as well as hydrogen described previously, carbon monoxide, ammonia, hydrazine, formaldehyde, and lower alcohols such as methanol. These reducing agents may be used alone or in a mixture. They may be used in a condition where they are diluted with inert gas such as nitrogen, helium and argon, or in the presence of a small amount of water. The reduction described above turns copper contained in the catalyst precursor of the present invention into reduced copper to reveal a catalyst activity.

(Production process for alcohol)

Organic carboxylic acid and/or organic carboxylic ester used for hydrogenation include alicyclic carboxylic acids, aromatic carboxylic acids, aliphatic carboxylic acids, and lower or higher alcohol esters of the above carboxylic acids. They are reduced in carboxylic acid parts by hydrogenation to form corresponding alcohols. They include, for example, linear or branched, saturated or unsaturated fatty acids having one or more carbons, esters of alcohols with the above fatty acids, alicyclic carboxylic acids, aromatic carboxylic acids, and esters of alcohols with the above carboxylic acids. An alcohol part in carboxylic ester shall not specifically be restricted. Examples of such carboxylic acids include formic acid, acetic acid, caproic acid, caprylic acid, capric acid, lauric acid, myristic acid, palmitic acid, stearic acid, isostearic acid, oleic acid, oxalic acid, maleic acid, adipic acid, sebacic acid, cyclohexanecarboxylic acid, benzoic acid, and phthalic acid. Examples of carboxylic esters include formic ester, acetic ester, caproic ester, caprylic ester, capric ester, lauric ester, myristic ester, palmitic ester, stearic ester, isostearic ester, oleic ester, oxalic ester, maleic ester, adipic ester, sebacic ester, cyclohexanecarboxylic ester, benzoic ester, and phthalic ester.

When the carboxylic acids and/or carboxylic esters described above are hydrogenated, any of a suspension reaction method, a fixed bed reaction method, and a fluidized bed reaction method is employed according to the catalyst form.

In the case where, for example, the suspension reaction method is employed, a powder catalyst is used. A solvent can be used for the reaction but in light of the productivity, the reaction is carried out preferably in a non-solvent condition. A solvent which does not exert an adverse effect on the reaction, such as alcohol, dioxane and hydrocarbon is selected. In this case, the catalyst amount is preferably 0.1 to 20% by weight based on the weight of carboxylic ester but can optionally be selected according to the reaction temperatures or reaction pressure in a range where the practical reaction rate can be obtained. The reaction temperatures are 160° to 350° C., preferably 200° to 300° C. The reaction pressure is 1 to 350 kg/cm², preferably 30 to 350 kg/cm². In the case where the fixed bed reaction method is employed, the molded catalyst is used. The reaction temperatures are 130° to 300° C., preferably 160° to 270° C. The reaction pressure is 0.1 to 300 kg/cm². The liquid space velocity (LHSV) is optionally determined according to the reaction conditions and falls preferably in a range of 0.5 to 5 in light of the productivity or the reactivity.

EXAMPLES

The present invention shall be explained below in detail with reference to examples, but the present invention shall by no means be restricted to these examples. The term "%" used in the following examples means "% by weight".

Example 1

(Preparation of the hydrogenation catalyst precursor) A reactor equipped with a reflux condenser was charged with 600 g of water, 96 g of $CuSO_4 \cdot 5H_2O$, 45.2 g of $FeSO_4 \cdot 7H_2O$, and 20.7 g of aluminum hydroxide (Hygilite H42M manufactured by Showa Denko Co., Ltd.), and the temperature was elevated up to 95° C. while stirring. Then, a solution prepared by dissolving 59.8 g of sodium carbonate in 212.3 g of water was dropwise added while maintaining this temperature. pH observed after finishing dropwise adding was 8.2. A solution prepared by dissolving 187.2 g of $Al_2(SO_4)_3 \cdot 16H_2O$ in 436.8 g of water and a solution prepared by dissolving 102.2 g of sodium carbonate in 362 g of water were dropwise added at the same time while maintaining the temperature at 95°±2° C. The pH value after dropwise adding the metal salt solutions was 8.8. Then, the temperature was lowered down to 60° C., and the slurry was filtered off by suction. The precipitate thus obtained was washed three times with 300 ml of water and then dried for a night in the air of 110° to 120° C. The matter obtained after finishing drying was slightly pulverized and calcined for one hour at 800° C. in the air to obtain a prescribed hydrogenation catalyst precursor. This hydrogenation catalyst precursor had an atomic ratio Cu/Fe/Al of 1/0.4/1.6.

An amount of copper-aluminum spinel was determined by the XANES method (X-ray absorption near edge structure method; measuring apparatus: EXAC-820 manufactured by Technos Co., Ltd.) to find that copper atoms having a copper-aluminum spinel structure had a proportion of 73% by weight based on the whole copper atoms contained in the hydrogenation catalyst precursor. Measurement by the XANES method was carried out in the following conditions after the hydrogenation catalyst precursor was diluted with about 300 mg of cellulose and molded into pellets having a diameter of 20 mm:

Measuring conditions (measuring apparatus: EXAC-820 manufactured by Technos Co., Ltd.)

| Spectral crystal | Ge (440) |
|---|---|
| Emission slit | 3.0 mm |
| Reception slit | 0.1 mm |
| X-ray source | 30 KV-100 mA |
| Measuring range (step) | 8950.0 to 9050.0 eV (0.5 eV) |

(Evaluation of catalyst activity and selectivity)

An autoclave of 500 cm³ was charged with 200 g of palm kernel fatty acid methyl ester (saponification value (SV)= 250 mg KOH/g) and 3 g of the hydrogenation catalyst precursor, and the reaction was carried out at a hydrogen pressure of 250 kg/cm² (gauge pressure), a reaction temperature of 285° C. and a stirring rate of 800 rpm under flow of hydrogen by a suspension reaction method. In this case, the first order reaction rate constant k (×100/minute) was calculated from the SV values according to lapse of time to make it an index for the catalyst activity. Further, the samples were analyzed according to lapse of time by means of capillary gas chromatography, and the analytical values were used to determine the ether compound content (%) and the hydrocarbon content (%) when the saponification value (SV) was 5 mg KOH/g to make them an index for a selectivity of the catalyst. The results thus obtained are shown in Table 1.

Examples 2 to 4

The hydrogenation catalyst precursors were obtained in the same manner as that in Example 1, except that the atomic ratios Cu/Fe/Al were changed as shown in Table 1. The catalyst precursors thus obtained were used to carry out the reaction evaluation according to the evaluation method used in Example 1. The results thereof are shown in Table 1.

Example 5

(Preparation of the hydrogenation catalyst precursor)

A reactor equipped with a reflux condenser was charged with 472 g of water, 48 g of $CuSO_4 \cdot 5H_2O$, 10.7 g of $FeSO_4 \cdot 7H_2O$, and 105.3 g of $Al_2(SO_4)_3 \cdot 16H_2O$, and the temperature was elevated up to 96° C. while stirring. Then, 369.6 g of 22% sodium carbonate was dropwise added while maintaining the temperature at 95°±2° C. pH observed after finishing dropwise adding was 9.8. Then, the temperature was lowered down to 60° C., and the slurry was filtered off by suction. The precipitate thus obtained was washed three times with 300 ml of water and then dried for a night in the air of 110° to 120° C. The matter obtained after finishing drying was slightly pulverized and calcined for one hour at 800° C. in the air to obtain a prescribed hydrogenation catalyst precursor. This hydrogenation catalyst precursor had an atomic ratio Cu/Fe/Al of 1/0.2/1.8.

An amount of copper-aluminum spinel was determined in the same manner as that in Example 1 to find that copper atoms having a copper-aluminum spinel structure had a proportion of 85% by weight based on the whole copper atoms contained in the hydrogenation catalyst precursor.

The resulting hydrogenation catalyst precursor was used to carry out the reaction evaluation according to the evaluation method used in Example 1. The results thereof are shown in Table 1.

Example 6

(Preparation of the hydrogenation catalyst precursor)

A reactor equipped with a reflux condenser was charged with 472 g of water, 48 g of $CuSO_4 \cdot 5H_2O$, 10.7 g of $FeSO_4 \cdot 7H_2O$, 105.3 g of $Al_2(SO_4)_3 \cdot 16H_2O$, and 17.7 g of titania (manufactured by Sakai Chemical Co., Ltd., BET specific surface area: 180 m²/g), and the temperature was elevated up to 95° C. while stirring. Then, 379 g of 22% sodium carbonate was dropwise added while maintaining the temperature at 95°±2° C. pH observed after finishing dropwise adding was 9.84. Then, the temperature was lowered down to 60° C., and the slurry was filtered off by suction. The precipitate thus obtained was washed three times with 300 ml of water and then dried for a night in the air of 110° to 120° C. The matter obtained after finishing drying was slightly pulverized and calcined for one hour at 800° C. in the air to obtain a prescribed hydrogenation catalyst precursor. This hydrogenation catalyst precursor had an atomic ratio Cu/Fe/Al of 1/0.2/1.8.

An amount of copper-aluminum spinel was determined in the same manner as that in Example 1 to find that copper atoms having a copper-aluminum spinel structure had a proportion of 85% by weight based on the whole copper atoms contained in the hydrogenation catalyst precursor.

The resulting hydrogenation catalyst precursor was used to carry out the reaction evaluation according to the evaluation method used in Example 1. The results thereof are shown in Table 1.

Example 7
(Preparation of the hydrogenation catalyst precursor)

A reactor equipped with a reflux condenser was charged with 472 g of water, 48 g of $CuSO_4 \cdot 5H_2O$, 10.7 g of $FeSO_4 \cdot 7H_2O$, and 105.3 g of $Al_2(SO_4)_3 \cdot 16H_2O$, and the temperature was elevated up to 96° C. while stirring. Then, 396.9 g of 22% sodium carbonate was dropwise added while maintaining the temperature at 95°±2° C. pH observed after finishing dropwise adding was 9.8. Then, the temperature was lowered down to 60° C., and the slurry was filtered off by suction. After the precipitate thus obtained was washed three times with 300 ml of water, a solution obtained by dissolving 1.4 g of barium carbonate in 20 g of water was added, and the slurry was dried up by evaporation after stirring for 30 minutes. The matter obtained after finishing drying was slightly pulverized and calcined for one hour at 800° C. in the air to obtain a prescribed hydrogenation catalyst precursor. This hydrogenation catalyst precursor had an atomic ratio Cu/Fe/Al/Ba of 1/0.2/1.8/0.037.

An amount of copper-aluminum spinel was determined in the same manner as that in Example 1 to find that copper atoms having a copper-aluminum spinel structure had a proportion of 85% by weight based on the whole copper atoms contained in the hydrogenation catalyst precursor.

The resulting hydrogenation catalyst precursor was used to carry out the reaction evaluation according to the evaluation method used in Example 1. The results thereof are shown in Table 1.

Example 8
(Preparation of the hydrogenation catalyst precursor)

A reactor equipped with a reflux condenser was charged with 472 g of water, 48 g of $CuSO_4 \cdot 5H_2O$, 10.7 g of $FeSO_4 \cdot 7H_2O$, 2.4 g of $ZnSO_4 \cdot 5H_2O$, and 105.3 g of $Al_2(SO_4)_3 \cdot 16H_2O$, and the temperature was elevated up to 96° C. while stirring. Then, 396.9 g of 22% sodium carbonate was dropwise added while maintaining the temperature at 95°±2° C. pH observed after finishing dropwise adding was 9.8. Then, the temperature was lowered down to 60° C., and the slurry was filtered off by suction. After the precipitate thus obtained was washed three times with 300 ml of water, a solution obtained by dissolving 1.4 g of barium carbonate in 20 g of water was added, and the slurry was dried up by evaporation after stirring for 30 minutes. The matter obtained after finishing drying was slightly pulverized and calcined for one hour at 800° C. in the air to obtain a prescribed hydrogenation catalyst precursor. This hydrogenation catalyst precursor had an atomic ratio Cu/Fe/Al/Zn/Ba of 1/0.2/1.8/0.05/0.037.

An amount of copper-aluminum spinel was determined in the same manner as that in Example 1 to find that copper atoms having a copper-aluminum spinel structure had a proportion of 85% by weight based on the whole copper atoms contained in the hydrogenation catalyst precursor.

The resulting hydrogenation catalyst precursor was used to carry out the reaction evaluation according to the evaluation method used in Example 1. The results thereof are shown in Table 1.

Comparative Examples 1 to 6

The hydrogenation catalyst precursors were obtained in the same manner as that in Example 1, except that the atomic ratios Cu/Fe/Al were changed as shown in Table 1. The catalyst precursors thus obtained were used to carry out the reaction evaluation according to the evaluation method used in Example 1. The results thereof are shown in Table 1.

Comparative Example 7

A commercial copper chromite catalyst was used to carry out the reaction evaluation according to the evaluation method used in Example 1. The results thereof are shown in Table 1.

TABLE 1

| Example and Comparative Example | Carrier | Carrier amount in catalyst precursor (%) | Constitutive Element | Atomic ratio (Cu/Fe/Al) | [(Cu atoms forming Cu—Al spinel/(whole Cu atoms in catalyst precursor)] × 100 (%) |
| --- | --- | --- | --- | --- | --- |
| Ex. 1 | Hygilite H42M | 15 | Cu/Fe/Al | 1/0.4/1.6 | 73 |
| Ex. 2 | Hygilite H42M | 15 | Cu/Fe/Al | 1/0.2/1.8 | 82 |
| Ex. 3 | Hygilite H42M | 15 | Cu/Fe/Al | 1/0.1/1.9 | 86 |
| Ex. 4 | Hygilite H42M | 15 | Cu/Fe/Al | 1/0.2/3.5 | 79 |
| Comp. Ex. 1 | Hygilite H42M | 15 | Cu/Fe/Al | 1/0.6/1.4 | 60 |
| Comp. Ex. 2 | Hygilite H42M | 15 | Cu/Fe/Al | 1/0.8/1.2 | 53 |
| Comp. Ex. 3 | Hygilite H42M | 15 | Cu/Fe/Al | 1/0.2/4.2 | 80 |
| Comp. Ex. 4 | Hygilite H42M | 15 | Cu/Fe/Al | 1/0.2/0.9 | 40 |
| Comp. Ex. 5 | Hygilite H42M | 15 | Cu/Al | 1/2 | 90 |
| Comp. Ex. 6 | Hygilite H42M | 15 | Cu/Fe | 1/2 | — |
| Comp. Ex. 7 | — | — | Cu/Cr/Mn | — | — |
| Ex. 5 | — | — | Cu/Fe/Al | 1/0.2/1.8 | 85 |
| Ex. 6 | $TiO_2$ | 33 | Cu/Fe/Al | 1/0.2/1.8 | 85 |
| Ex. 7 | — | — | Cu/Fe/Al/Ba | 1/0.2/1.8 | 85 |
| Ex. 8 | — | — | Cu/Fe/Al/Zn/Ba | 1/0.2/1.8 | 85 |

TABLE 1-continued

| Example and Comparative Example | Calcining temperature /hour | Reaction evaluation results | | |
|---|---|---|---|---|
| | | Reaction rate constant | Reaction selectivity | |
| | | k (×100/min) | Hydrocarbon (%) | Ether compound content (%) |
| Ex. 1 | 800° C./1 hr | 7.50 | 0.14 | 0.020 |
| Ex. 2 | 800° C./1 hr | 8.00 | 0.13 | 0.020 |
| Ex. 3 | 800° C./1 hr | 7.80 | 0.13 | 0.040 |
| Ex. 4 | 800° C./1 hr | 7.50 | 0.13 | 0.020 |
| Comp. Ex. 1 | 800° C./1 hr | 6.60 | 0.15 | 0.020 |
| Comp. Ex. 2 | 860° C./1 hr | 5.90 | 0.14 | 0.017 |
| Comp. Ex. 3 | 800° C./1 hr | 6.40 | 0.13 | 0.020 |
| Comp. Ex. 4 | 800° C./1 hr | 4.90 | 0.13 | 0.030 |
| Comp. Ex. 5 | 800° C./1 hr | 6.60 | 0.27 | 1.050 |
| Comp. Ex. 6 | 800° C./1 hr | 1.90 | 3.50 | 0.020 |
| Comp. Ex. 7 | — | 6.70 | 0.13 | 0.030 |
| Ex. 5 | 800° C./1 hr | 11.20 | 0.20 | 0.040 |
| Ex. 6 | 800° C./1 hr | 10.50 | 0.20 | 0.040 |
| Ex. 7 | 800° C./1 hr | 11.00 | 0.19 | 0.020 |
| Ex. 8 | 800° C./1 hr | 10.80 | 0.10 | 0.020 |

What is claimed is:

1. A hydrogenation catalyst precursor comprising copper, iron and aluminum and containing a compound oxide of copper, iron and aluminum having an atomic ratio Cu:Fe:Al of 1:(0.02 to 0.4):(1.0 to 4.0) and having a copper-aluminum spinel structure.

2. The hydrogenation catalyst precursor as described in claim 1, wherein copper atoms forming the copper-aluminum spinel structure have a proportion exceeding 65% by weight based on the total weight of copper atoms contained in the hydrogen catalyst precursor.

3. The hydrogenation catalyst precursor as described in claim 1 or 2, further and optionally comprising barium and/or zinc and having an atomic ratio Cu:Ba:Zn of 1:(0 to 2.0):(0 to 2.0).

4. The hydrogenation catalyst precursor as described in claim 1, obtainable by a solid phase reaction of copper oxide with aluminum oxide at calcining temperatures of 500° to 1500° C.

5. A hydrogenation catalyst obtained by reducing the hydrogenation catalyst precursor as described in claim 1.

6. A production process for alcohols, comprising catalytically reducing organic carboxylic acid and/or organic carboxylic ester in the presence of the hydrogenation catalyst as described in claim 5.

7. The hydrogenation catalyst precursor as described in claim 2, obtainable by a solid phase reaction of copper oxide with aluminum oxide at calcining temperatures of 500° to 1500° C.

8. The hydrogenation catalyst precursor as described in claim 3, obtainable by a solid phase reaction of copper oxide with aluminum oxide at calcining temperatures of 500° to 1500° C.

9. A hydrogenation catalyst obtained by reducing the hydrogenation catalyst precursor as described in claim 2.

10. A hydrogenation catalyst obtained by reducing the hydrogenation catalyst precursor as described in claim 3.

11. A hydrogenation catalyst obtained by reducing the hydrogenation catalyst precursor as described in claim 4.

12. A hydrogenation catalyst obtained by reducing the hydrogenation catalyst precursor as described in claim 7.

13. A hydrogenation catalyst obtained by reducing the hydrogenation catalyst precursor as described in claim 8.

14. A production process for alcohols, comprising catalytically reducing organic carboxylic acid and/or organic carboxylic ester in the presence of the hydrogenation catalyst as described in claim 9.

15. A production process for alcohols, comprising catalytically reducing organic carboxylic acid and/or organic carboxylic ester in the presence of the hydrogenation catalyst as described in claim 10.

16. A production process for alcohols, comprising catalytically reducing organic carboxylic acid and/or organic carboxylic ester in the presence of the hydrogenation catalyst as described in claim 11.

17. A production process for alcohols, comprising catalytically reducing organic carboxylic acid and/or organic carboxylic ester in the presence of the hydrogenation catalyst as described in claim 12.

18. A production process for alcohols, comprising catalytically reducing organic carboxylic acid and/or organic carboxylic ester in the presence of the hydrogenation catalyst as described in claim 13.

* * * * *